(12) United States Patent
Ziff

(10) Patent No.: US 6,241,328 B1
(45) Date of Patent: Jun. 5, 2001

(54) ENCLOSED WORKSTATION

(76) Inventor: David Ziff, 1822 Hillcrest St., Orlando, FL (US) 32803

( * ) Notice: Subject to any disclaimer, the term of this patent is extended or adjusted under 35 U.S.C. 154(b) by 0 days.

(21) Appl. No.: 09/534,375

(22) Filed: Mar. 24, 2000

(51) Int. Cl.$^7$ ................................................ A61G 11/00
(52) U.S. Cl. ........................ 312/1; 312/292; 312/209
(58) Field of Search .................... 312/1, 3, 4, 5, 312/6, 114, 119, 209, 211, 291, 292, 229, 902, 129, 293.2, 283, 284, 138.1; 211/70.6

(56) References Cited

U.S. PATENT DOCUMENTS

| | | | |
|---|---|---|---|
| 1,539,051 | * 5/1925 | McLean | 312/229 X |
| 2,561,125 | * 7/1951 | Leibowitz | 312/292 X |
| 2,624,333 | * 1/1953 | Dixon et al. | 312/3 X |
| 2,651,982 | * 9/1953 | Weaver | 312/1 X |
| 2,786,740 | * 3/1957 | Taylor et al. | 312/1 |
| 2,962,156 | * 11/1960 | Adams | 312/902 X |
| 3,084,684 | 4/1963 | Saunders . | |
| 3,498,687 | * 3/1970 | Diccianni | 312/1 |
| 4,059,903 | 11/1977 | Piet et al. . | |
| 4,130,326 | * 12/1978 | Hornblad | 312/292 |
| 4,697,854 | 10/1987 | Lunsford | 312/223.5 |
| 4,730,880 | 3/1988 | Schmidt et al. | 312/209 |
| 4,834,357 | 5/1989 | Bodenmiller | 312/209 X |
| 5,011,013 | * 4/1991 | Meisner et al. | 312/902 X |
| 5,095,925 | 3/1992 | Elledge et al. | 134/61 |
| 5,170,027 | 12/1992 | Brodersen | 312/1 X |
| 5,316,733 | * 5/1994 | Rune et al. | 312/1 X |
| 5,380,077 | 1/1995 | Püschner | 312/1 |
| 6,058,523 | * 5/2000 | Sleboda | 312/292 X |

FOREIGN PATENT DOCUMENTS

2833465 * 2/1980 (DE) ........................................ 312/1

* cited by examiner

Primary Examiner—Peter M. Cuomo
Assistant Examiner—James O. Hansen
(74) Attorney, Agent, or Firm—Brian S. Steinberger; Law Offices of Brian S. Steinberger

(57) ABSTRACT

A self-enclosed workstation box having side access ports with built-in sleeve guards, a removable viewing shield, a pull-out precious metal material/waste recovery drawer, a storage bin inside of the box with a holder on the bin cover for storing and supporting tools thereon. The viewing shield can be hinged to the box for allowing access to the entire interior of the box. The shield can have a slidable and removable window door for allowing a smaller access than opening the entire shield. The recovery drawer can slide out from underneath the box by a handle grip. Above the drawer can be a longitudinal slot running the length of the drawer for allowing precious metal materials and waste materials to be moved to fall into the drawer. The storage bin can have a divider wall for forming separate compartments therein. The bin cover can be hingedly connected to the bin and have parallel racks with indentations for allowing plural tools to be stored thereon for easy accessibility to the operator.

13 Claims, 6 Drawing Sheets

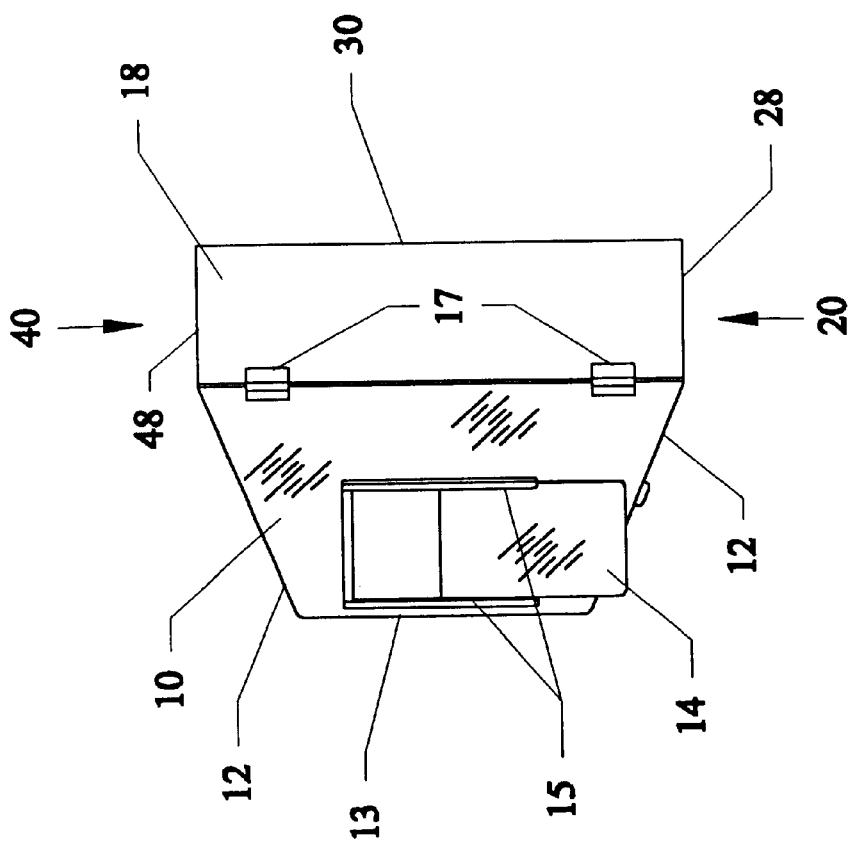
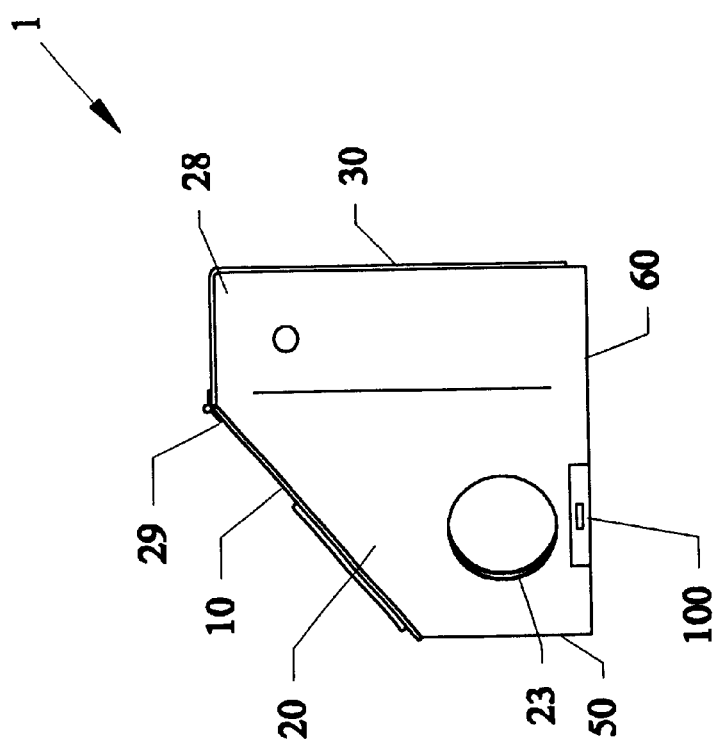
Fig. 4
Fig. 3

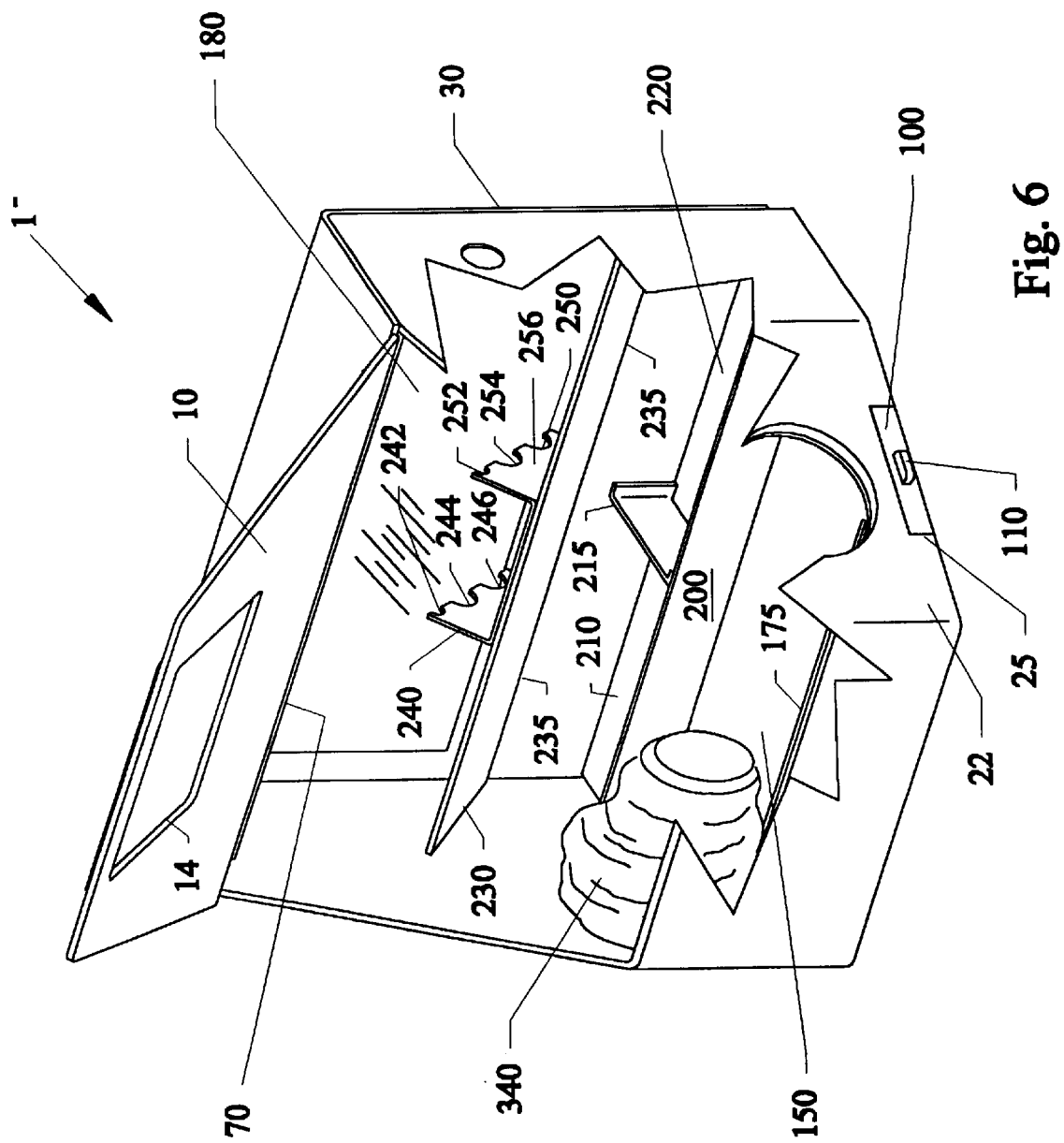

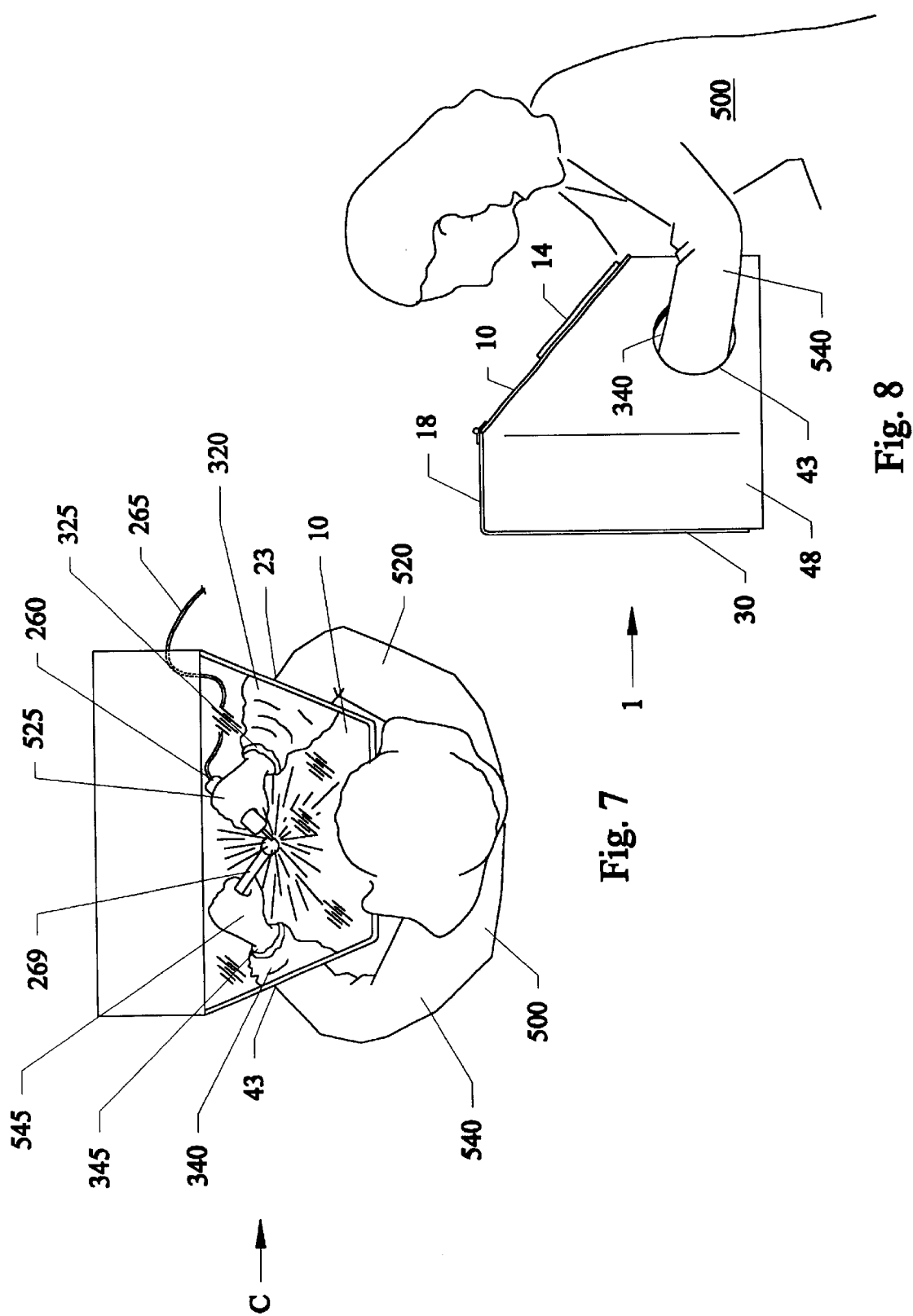

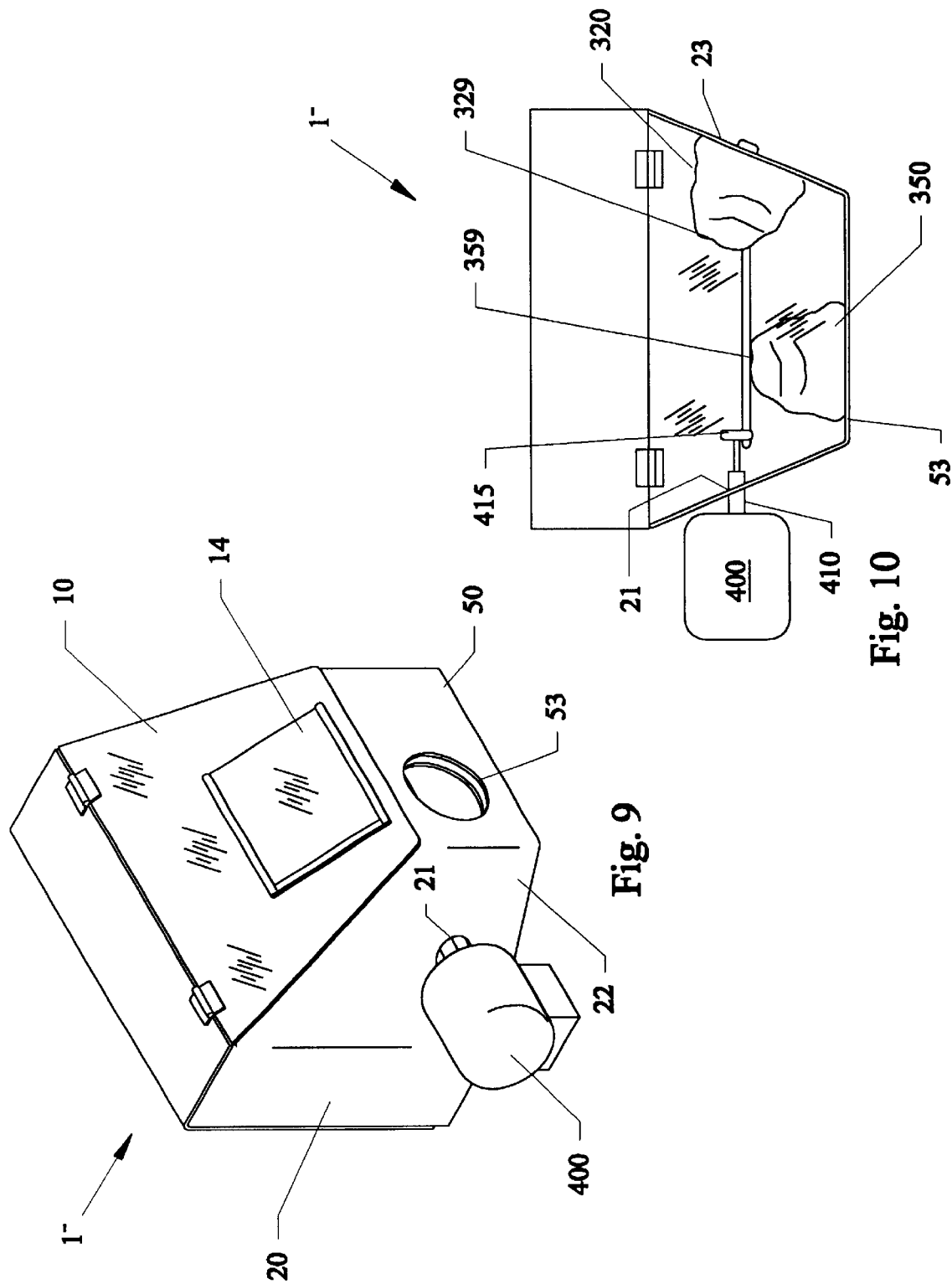

ENCLOSED WORKSTATION

This invention relates to enclosures for workstations, and in particular to a see-through enclosure that allows one to grind and refine dental restorations in a totally enclosed environment.

BACKGROUND AND PRIOR ART

The machining of dental pieces often requires rotary type tools that produce significant risks to the operator of the tools. For example, the dust and metal grindings that often are produced can be harmful if breathed by the operator. Thus, facemasks are needed if the machining takes place in an open environment. Also, eye protection, such as goggles would be needed since flying debris can be dangerous to the operator's eyes. Furthermore, it is even necessary to wear protective garments to further protect the clothes and body of the operator from flying debris. For example, to use the types of workstations described in U.S. Pat. No. 4,730,880 to Schmidt et al.; U.S. Pat. No. 4,834,357 to Bodenmiller would require all these types of protection.

There are many problems associated with using all of this protection. For example, using eye-protection, face masks, gloves, and protective garments are both uncomfortable to wear and make the tooling operation even more difficult. Additionally, replacing the eye-protection, masks, gloves and protective garments is an additional expense since these materials wear out over time.

The flying debris from using the tools causes dust, grindings, and other waste material to be sprayed all over the entire office area. The operator then has the added time burden and labor expense of having to clean the workstation areas and surrounding room space. This problem becomes compounded if some of the grindings are valuable metals and materials that could have been recycled, and/or reclaimed.

There have been several proposals over time to overcome the problems presented above. See for example, U.S. Pat. No. 3,084,684 to Saunders; U.S. Pat. No. 4,059,903 to Piet et al.; U.S Pat. No. 4,697,854 to Lunsford; U.S. Pat. No. 5,095,925 to Elledge et al.; U.S. Pat. No. 5,170,027 to Brodersen; and U.S. Pat. No. 5,380,077 to Puschner et al.

However, several of these inventions require expensive and elaborate components that are large and cumbersome and must be floor mounted or supported by specialized carts. See for example, U.S. Pat. No. 4,697,854 to Lunsford; and U.S. Pat. No. 5,170,027 to Brodersen. Still furthermore, many of these devices use vacuum lines and filters, if any to pull in waste dust. None of these cited patents do allow for any easy access to removing all of the waste materials. Additionally, none of these patents describe an easily accessible storage rack for holding and storing tools between operations within the enclosure. Still furthermore, none of the enclosed workstations use any magnification glasses to magnify the work being performed in order to help the operator.

SUMMARY OF THE INVENTION

The first objective of this invention is to provide a self-enclosed work station that eliminates the need for a tool operator to wear protective eyewear, facemasks, gloves, and protective garments.

The second object of the present invention is to provide a self-enclosed work station that does not need to be floor mounted and can be used on a bench.

The third object of the present invention is to provide a self-enclosed work station that allows an operator to perform grinding on a dental piece in a simple, non complex environment.

The fourth object of the present invention is to provide a self-enclosed work station that confines all resultant dust, and waste within the enclosure and allows for easy removal of the resultant dust and waste.

The fifth object of the present invention is to provide a self-enclosed workstation having a recovery drawer for allowing for easy and complete reclamation of precious metals.

The sixth object of this invention is to provide a self-enclosed workstation that allows the operator to hold and store their tools within the workstation in easily accessible racks.

The seventh object of this invention is to provide a self-enclosed workstation that uses a removable magnifying viewing window to magnify the work being performed and an internal light source.

A preferred embodiment of the self-enclosed workstation can include a box having side access ports with sealable sleeve guards for allowing an operator to position bare hands or gloved hands inside the box through sleeve/cuff guards having elastic constricting wrist openings. A viewing shield cover on top of the box can include a removable slidable access door. The shield can openly pivot to allow full access inside the box and the slidable door can allow a smaller access opening into the box. The shield and/or the slidable door can be made from a magnifying lens material. A material recovery drawer can include a handle for allowing the drawer to slide out from underneath of the workstation, and a longitudinal slot can be located through an interior floor section over the drawer so that the slot is underneath and substantially in length to the depth of the drawer. The drawer can be used for allowing precious metals and even waste materials to be reclaimed completely with ease. A storage bin can be located inside of the box for storing components and have a removable lid on top of the storage bin for supporting tools thereon. The storage bin can have a divider for separating the storage bin into compartments. The lid can have a rack for storing and holding plural tools thereon. The box can include other features such as a rear mounted mirror, an interior light, and side sleeve guards having for allowing operators with bare hands or gloved hands to use the box. The box can allow for the messy operations of grinding and polishing acrylics, while containing all of the materials within one enclosure.

Further objects and advantages of this invention will be apparent from the following detailed description of a presently preferred embodiment which is illustrated schematically in the accompanying drawings.

BRIEF DESCRIPTION OF THE FIGURES

FIG. 3 is another side view of the workstation of FIG. 1 along arrow B.

FIG. 4 is a top view of the shield of FIG. 1, with a slide access door in an open position.

FIG. 6 is another view of FIG. 5 with the side precious metal material/waste recovery drawer in an open position.

FIG. 7 is a top view of the workstation of the preceding figures with an operator.

FIG. 8 is a side view of the workstation and operator of FIG. 7 along arrow C.

FIG. 9 is another perspective view of the workstation of the preceding figures with an attached grinding tool, and one glove access port in front of the workstation.

FIG. 10 is a top view of the workstation of FIG. 9.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 2:
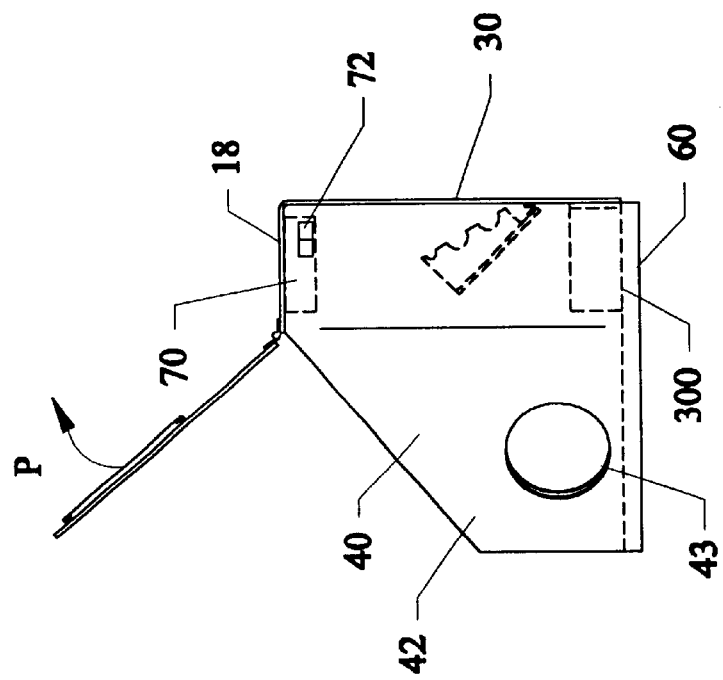
FIG. 2 is a side view of the workstation of FIG. 1 along arrow A, with the shield in an open position.
Figure 1:
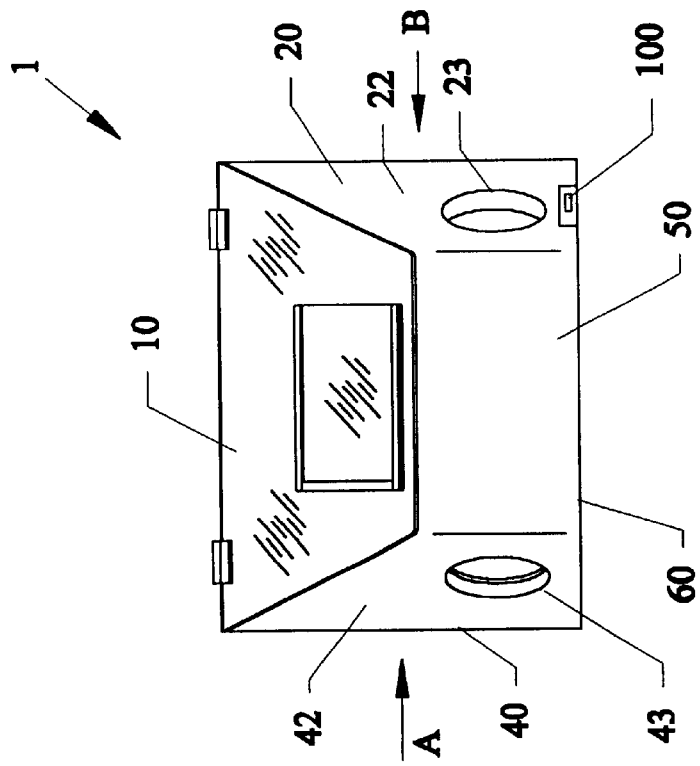
FIG. 1 shows a front view of a novel enclosed workstation invention.

FIG. 1 shows a front view of a novel enclosed workstation invention 1. FIG. 2 is a side view of the workstation 1 of FIG. 1 along arrow A, with the shield 10 in an open position. FIG. 3 is another side view of the workstation 1 of FIG. 1 along arrow B. FIG. 4 is a top view of the shield 10 of FIG. 1, with a slide access door 15 in an open position. Referring to FIGS. 1–4, workstation 1 includes angled viewing shield 10 which can be angled at approximately forty-five degrees downward from a planar top cover 18. Viewing shield 10 can be a see-through glass, a magnifying type lens, and the like. Shield 10 can have a larger upper rear end 11 with a hinged edge 17 for allowing a large access opening to the interior of the workstation by allowing the shield to pivot about hinges 17 in the direction of arrow P. Shield 10 includes angled sides 12, and a smaller front end 13 than the rear end 11. A slideable removable access window door 14 can slide within tracks 15 for allowing a smaller access opening to the interior of the workstation than opening the entire shield 10. The viewing window 14 can be a magnifying lens that can be separately removed and replaced. The workstation 1 can be used without the viewing window 14 as an unscratchable viewing portal. The smaller access opening 14 can be useful to manipulate components inside of the workstation without having to open the entire shield 10. Workstation 1 can be generally box like with the rear portion 18, 48, 30, and 28 being generally rectangular, with the front portions 22, 50, 42 being angled inwardly toward the front wall 50. Viewing shield 10 can be a clear material such as but not limited to Plexiglas, acrylic and the like, for allowing an operator to view inside. Also all of the exterior sides 20, 30, 40 and 50 of the workstation can be formed from a clear material so that all interior areas of the workstation can be visible to an operator. Additionally, the enclosure can include sides and a bottom that can be formed from other materials such as but not limited to aluminum, galvanized metal, stainless steel, hardened plastic, combinations thereof, and the like. The planar base 60 of the workstation 1 allows the workstation to be supported on any flat surface such as but not limited to a worktable, a shelf, and the like.

Underneath planar top cover 18, can be a light 70 such as a conventional fluorescent bulb, and the like. A simple exterior toggle switch 72 can turn on the light 70 when needed. On both sides 22, 42 of workstation 1 can be left and right arm access ports 23, 43, respectively, which will be described in greater detail in reference to the other figures.

Figure 5:
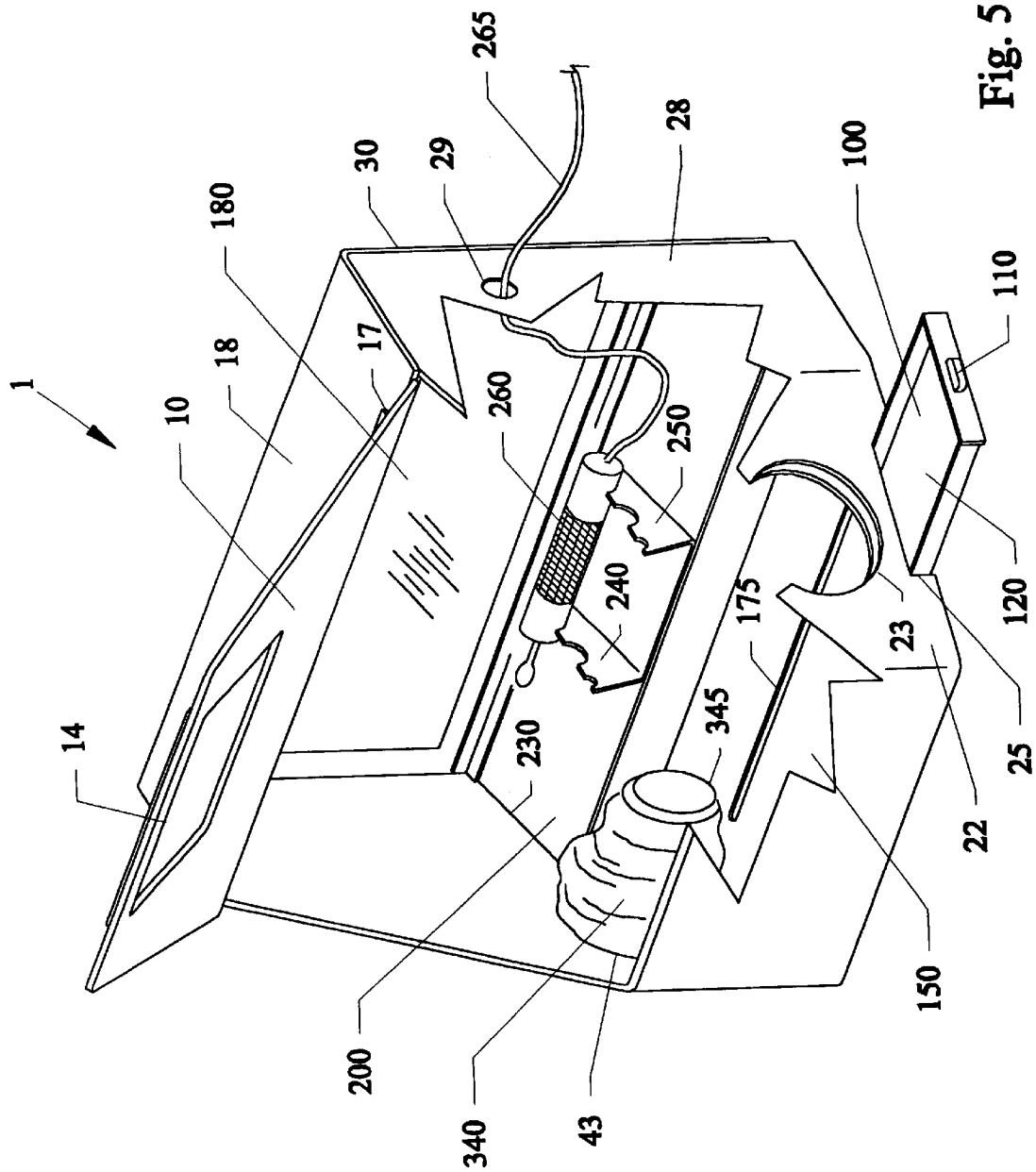
FIG. 5 is an enlarged perspective view of the workstation of FIG. 1, with the shield in an open position, and a partial cutout of the interior of the workstation, with interior storage bin.

FIG. 5 is an enlarged perspective view of the workstation 1 of FIG. 1, with the shield in an open position, and a partial cutout of the interior of the workstation, with interior storage bin. FIG. 6 is another view of FIG. 5 with the side precious metal material/waste recovery drawer 100 in an open position. The drawer 100 allows for the easy and complete reclamation of precious metal type materials and/or waste material. Referring to FIGS. 5–6, drawer 100 includes an exterior handle 110 and an interior compartment 120. The drawer 100 slides in and out of a side opening 25 in side portion 22, so that the drawer compartment 120 is substantially underneath a longitudinal slot 175 running along the interior floor 150 of the workstation 1. Along an upper portion of the rear wall 30 of the workstation 1 can be a mirror 180 that allows the operator better viewing capability within the workstation 1.

Inside of the workstation 1, can be a rectangular storage bin 200 located in a rear readily accessible portion on the floor 150, the bin running along the entire back wall 30 of the workstation 1. Inside the storage bin 200 can be at least one dividing wall 215 that allows the interior of the bin 200 to be divided into different storage compartment 210, 220 for allowing supplies, small tools, and the like to be separated and safely stored when not being used. On top of rear storage bin 200 can be a removable coverlid 230 that can pivot about hinges 235 allowing access within the bin 200. On top of coverlid 230 can be storage racks 240, 250. The racks 240, 250 can be parallel to one another and include various sized rounded indentations 242, 244, 246, 252, 254, 256 for allowing various sized handheld tools 260(only one is shown for clarity) to be supported and stored thereon, for easy accessibility. A handheld tool 260 such as a high speed rotary power tool can be powered by an outside powersources such as a 120 volt household power supply(not shown) by feeding a power cord 265 through a side port opening 29 in side wall 28 of the workstation 1.

FIG. 7 is a top view of the workstation 1 of the preceding figures with an operator 500. FIG. 8 is a side view of the workstation 1 and operator 500 of FIG. 7 along arrow C. Referring to FIGS. 1–8, an operator 500 can position their left arm 540 with a barehand or a pre-gloved hand 545 through left access port 43 and through a flexible sleeve guard 340, the latter being sealingly secured to the left access port 43. The inside of flexible sleeve guard 340 opens to a narrow elastic wrist band portion 345 which can stretch about and tighten about the wrist portion of the operator's left barehand/glove 545. The operator 500 can also position their right arm 520 with a barehand or pre-gloved hand 520 through the right access port 43 and through a flexible sleeve guard 320, the latter being sealingly secured to the right access port 23. The inside of flexible sleeve guard 320 opens to a narrow elastic wrist band portion 325 which can stretch about and tighten about the wrist portion of the operator's right barehand/glove 525. In FIGS. 7–8, the operator 500 can grip a workpiece 269 with the left hand 545 and grip a power tool 260 with the right hand 525.

The elastic narrow wrist bands 325, 345, allow the operator to only have to wear at most a pair of gloves 525, 545 when using the workstation 1. The operator 500 can choose to use the workstation 1, without gloves 525, 545, when less harmful operations are being performed within the workstation 1 and/or for allowing for greater tactile response.

FIG. 9 is another perspective view 1' of the workstation 1 of the preceding figures with an attached grinding tool 400. FIG. 10 is a top view 1' of the workstation 1 of FIG. 9. Referring to FIGS. 9–10, a tool 400 such as but not limited to a bench mounted rotary grinding tool, can be connected to the left side 20 of the workstation 1' by having its' rotatable arm 410 with grinding wheel 415 where the arm is positioned through a small access port 21 in the left side 20 of the workstation 1'. A front arm access port 53 in front wall 50 can include a built in elastic sleeve guard 350 similar to those previously described for allowing an operator's left hand to be inserted therein. With the right sleeve guard 320, the operator 500 can use the side mounted tool 400. Additionally, the right and left sleeve guards 350, 320 can have closed glove interior ends 359, 329 that can be shaped like mittens, and the like, to allow the operator to use the workstation 1' without exterior gloves. Similarly, the previous figures can be used with built in mitten sleeve guards as well. The embodiment in FIGS. 9 and 10, allows for the grinding of materials such as acrylic which can be very messy. Additionally, the embodiment allows for the polishing of materials such as acrylic and metals, while containing all of the mess within the enclosure 1'.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A self-enclosed workstation, comprising:
   a box having side access ports each with sleeve guards;
   a see-through viewing shield cover on top of the box;
   a work surface in the box between the side access ports;
   a storage bin inside of the box behind the worksurface for storing components therein;
   a removable lid on top of the storage bin, the lid having an upper surface with means for supporting tools thereon so that the tools are accessible while the lid is closed over the storage bin; and
   a material recovery drawer that slides out from underneath the box.

2. The self-enclosed workstation of claim 1, wherein the storage bin includes:
   a divider for separating the storage bin into compartments.

3. The self-enclosed workstation of claim 1, wherein the means for supporting the tools on the upper surface of the lid includes:
   a rack for storing and holding plural tools thereon.

4. The self-enclosed workstation of claim 1, further comprising:
   a see-through slidable access door on the shield for allowing a portion of the shield to slide to allow access within the workstation.

5. The self-enclosed workstation of claim 4, wherein the see-through slidable access door includes:
   a magnifying lens.

6. The self-enclosed workstation of claim 4, wherein the viewing shield cover further includes:
   a hinged edge for allowing the shield cover to pivot to an open position allowing greater access to the interior of the workstation than the slideable access door.

7. The self-enclosed workstation of claim 1, wherein the material recovery drawer includes:
   a longitudinal slot in an interior floor section over the drawer, the slot being substantially similar to the depth of the drawer.

8. The self-enclosed workstation of claim 1, wherein each of the sleeve guards includes:
   a flexible sleeve that opens to a narrow wrist band portion that can stretch about and tighten about a wrist portion of a hand.

9. A self-enclosed workstation, comprising:
   a box having side access ports each with sleeve guards;
   a see-through viewing shield cover on top of the box, the cover being able to open to allow access to inside of the box;
   a see-through slidable door in the viewing shield cover;
   a work surface in the box between the side access ports;
   a storage bin inside of the box behind the work surface for storing components inside; and
   a lid on top of the storage bin, the lid having an upper surface with a rack for storing and holding plural tools on top of the lid so that the tools are accessible while the lid is closed over the storage bin.

10. The self-enclosed workstation of claims 9, wherein the slidable door includes:
    a magnifying lens.

11. The self-enclosed workstation of claim 9, wherein the storage bin includes:
    a divider for separating the storage bin into compartments.

12. The self-enclosed workstation of claim 9, wherein each of the sleeve guards includes:
    a flexible sleeve that opens to a narrow wrist band portion that can stretch about and tighten about a wrist portion of a hand.

13. A self-enclosed workstation, comprising:
    a box having side access ports each with sleeve guards;
    a see-through viewing shield cover on top of the box;
    a work surface in the box between the side access ports;
    a storage bin inside of the box behind the worksurface for storing components therein; and
    a removable lid on top of the storage bin, the lid having an upper surface with a rack for supporting tools thereon so that the tools are accessible while the lid is closed over the storage bin.

* * * * *